United States Patent
Hsieh

Patent Number: 6,115,447
Date of Patent: Sep. 5, 2000

[54] MULTI-SLICE BIOPSY WITH SINGLE SLICE COMPUTED TOMOGRAPHY

[75] Inventor: Jiang Hsieh, Waukesha, Wis.

[73] Assignee: General Electric Company, Milwaukee, Wis.

[21] Appl. No.: 08/965,948

[22] Filed: Nov. 7, 1997

[51] Int. Cl.$^7$ .................................................. G01N 23/00
[52] U.S. Cl. ................................................ 378/19; 378/4
[58] Field of Search ........................................... 378/19, 4

[56] References Cited

U.S. PATENT DOCUMENTS

| | | | |
|---|---|---|---|
| 5,734,691 | 3/1998 | Hu et al. ...................................... | 378/19 |
| 5,841,831 | 11/1998 | Hell et al. .................................... | 378/19 |

*Primary Examiner*—Craig E. Church
*Attorney, Agent, or Firm*—Armstrong Teasdale; Christian G. Cabou; Phyllis Y. Price

[57] ABSTRACT

A method for controlling operation of a pre-patient collimator to sweep x-rays across a patient are described. Particularly, and rather than shuttling the patient back and forth to obtain scans of different locations, the x-ray beams are swept across the patient by adjusting the positions of the pre-patient collimator. The x-ray beam deviates from the nominal position in z (z is the axis perpendicular to the scan plane). Since the pre-patient collimator is very light, and since the amount of motion in collimator is very small due to the large magnification, the x-ray beam deflection can occur instantaneously without any ramp-up or ramp down periods. Therefore, a 100% duty cycle can be achieved and the image update rate may be reduced. Also, no modification to the reconstruction process is necessary. The nominal slice location for each reconstructed image can be easily estimated by the centroid of the beam location during the date acquisition.

20 Claims, 2 Drawing Sheets

MULTI-SLICE BIOPSY WITH SINGLE SLICE COMPUTED TOMOGRAPHY

FIELD OF THE INVENTION

This invention relates generally to computed tomography (CT) imaging and more particularly, to improving the quality of object scanning and image displays during interventional procedures using CT imaging.

BACKGROUND OF THE INVENTION

In at least one known CT system configuration, an x-ray source projects a fan-shaped beam which is collimated to lie within an X-Y plane of a Cartesian coordinate system, generally referred to as the "imaging plane". The x-ray beam passes through the object being imaged, such as a patient. The beam, after being attenuated by the object, impinges upon an array of radiation detectors. The intensity of the attenuated beam radiation received at the detector array is dependent upon the attenuation of the x-ray beam by the object. Each detector element of the array produces a separate electrical signal that is a measurement of the beam attenuation at the detector location. The attenuation measurements from all the detectors are acquired separately to produce a transmission profile.

In known third generation CT systems, the x-ray source and the detector array are rotated with a gantry within the imaging plane and around the object to be imaged so that the angle at which the x-ray beam intersects the object constantly changes. A group of x-ray attenuation measurements, i.e., projection data, from the detector array at one gantry angle is referred to as a "view". A "scan" of the object comprises a set of views made at different gantry angles during one revolution of the x-ray source and detector. In an axial scan, the projection data is processed to construct an image that corresponds to a two dimensional slice taken through the object.

One method for reconstructing an image from a set of projection data is referred to in the art as the filtered back projection technique. This process converts the attenuation measurements from a scan into integers called "CT numbers" or "Hounsfield units", which are used to control the brightness of a corresponding pixel on a cathode ray tube display.

To reduce the total scan time required for multiple slices, a "helical" scan may be performed. To perform a "helical" scan, the patient is moved in the z-axis synchronously with the rotation of the gantry, while the data for the prescribed number of slices is acquired. Such a system generates a single helix from a fan beam helical scan. The helix mapped out by the fan beam yields projection data from which images in each prescribed slice may be reconstructed. In addition to reduced scanning time, helical scanning provides other advantages such as better control of contrast, improved image reconstruction at arbitrary locations, and better three-dimensional images.

Efforts have been undertaken to enhance the quality of CT system support for interventional procedures such as biopsies. Significant support issues include the amount of time necessary to scan and display an image, and the quality of the displayed image. Particularly, and with respect to interventional procedures, images are not displayed in "real time," i.e., a lag exists between data acquisition, or scanning, and image display. Furthermore, known CT fluoroscopy systems typically are configured to scan at a fixed location, and display only one image slice at a time. Since the interventional procedure only proceeds as fast as the CT system acquires and displays data, such interventional procedures are done on a step-by-step, or display-by-display basis, rather than a continuing basis.

It is desirable to cover the volume (rather than a single slice) on a continuous basis. Particularly, the biopsy needle may not be perfectly aligned with the slice plane. As a result, the needle tip could protrude into the adjacent plane and not be monitored if only a single slice is covered. Also, volume data can be displayed with a 3D needle and provides the operator with depth information. To cover a volume, helical scans can be used. However, certain downtime will be encountered for the patient table to accelerate/decelerate since the patient is being moved back and forth. Of course, stationary volume scans can be achieved with multi-slice scanners. However, significant hardware/software changes become necessary.

It would be desirable to improve CT support for interventional procedures. Particularly, it would be desirable to acquire data, reconstruct such data and display an image for such data quickly enough to guide an interventional procedure. It also would be desirable to reduce any down time during an interventional procedure, and improve the image display for interventional procedures.

SUMMARY OF THE INVENTION

These and other objects may be attained by a method for controlling operation of a pre-patient collimator to swell x-rays across the patient. Particularly, and rather than shuttling the patient back and forth to obtain scans of different locations, the x-ray beams are swept across the patient by adjusting the positions of the pre-patient collimator. The x-ray beam deviates from the nominal position in z (z is the axis perpendicular to the scan plane).

Since the pre-patient collimator is very light, and since the amount of motion in collimator is very small due to the large magnification, the x-ray beam deflection can occur instantaneously without any ramp-up or ramp down periods. Therefore, a 100% duty cycle can be achieved and the image update rate may be reduced. Also, no modification to the reconstruction process is necessary. The nominal slice location for each reconstructed image can be easily estimated by the centroid of the beam location during the date acquisition.

DETAILED DESCRIPTION

Figure 1:
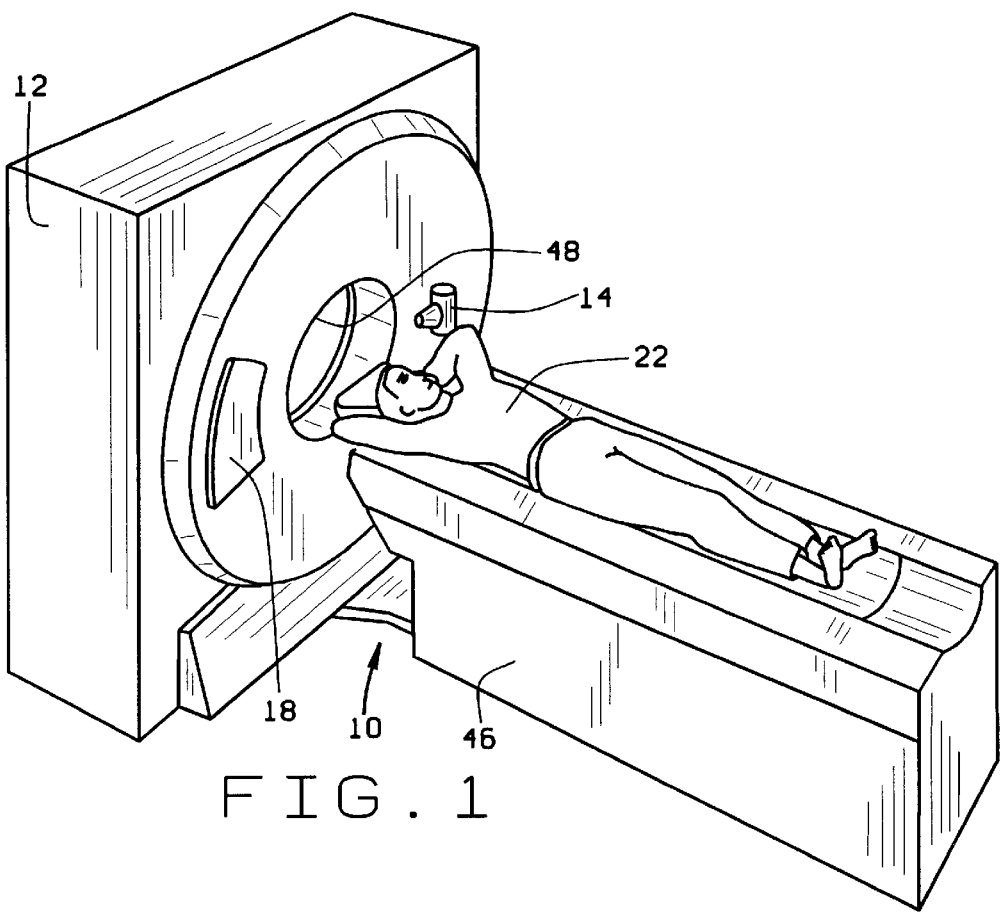
FIG. 1 is a pictorial view of a CT imaging system.
Figure 2:
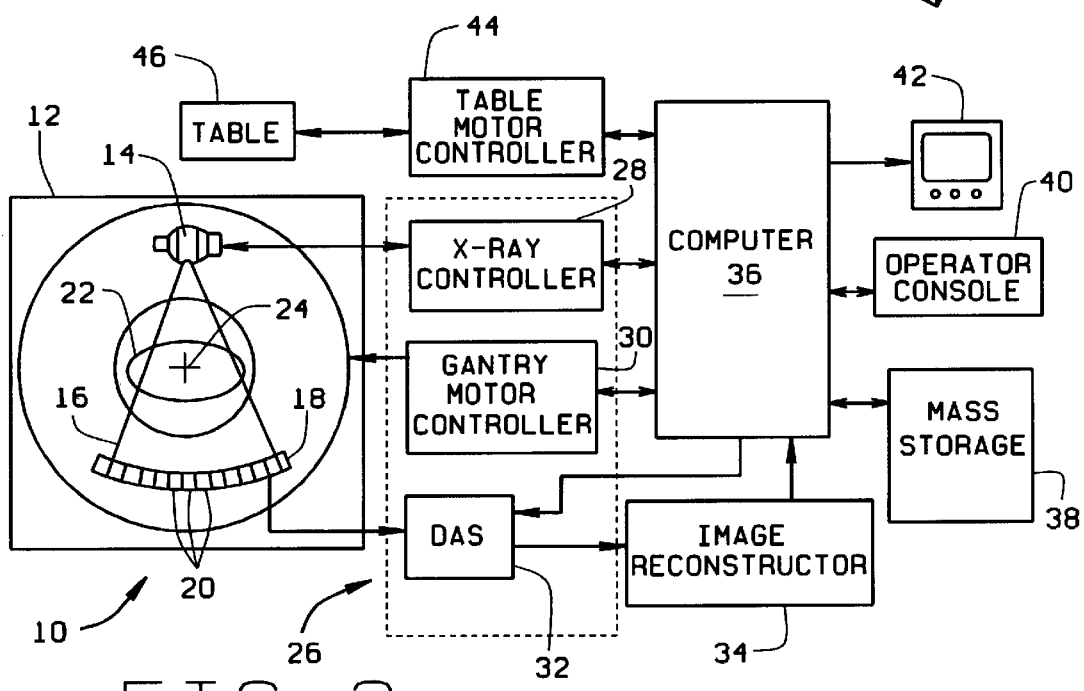
FIG. 2 is a block schematic diagram of the system illustrated in FIG. 1.

Referring to FIGS. 1 and 2, a computed tomograph (CT) imaging system 10 is shown as including a gantry 12 representative of a "third generation" CT scanner. The present invention is not limited to practice in connection with third generation scanners and can be used, for example, in fourth generation scanners and in CT electron beam type scanners. Therefore, although the present invention is sometimes described herein in connection with third generation scanners, it should be understood that such description is by way of example only, and not by way of limitation.

With respect to system 10, gantry 12 has an x-ray source 14 that projects a beam of x-rays 16 through a source collimator (not shown) and at a gantry angle (not shown) toward a detector array 18 on the opposite side of gantry 12.

Detector array 18 is formed by detector elements 10 which together sense the projected x-rays that pass through a medical patient 22. Each detector element 20 produces an electrical signal that represents the intensity of an impinging x-ray beam and hence the attenuation of the beam as it passes through patient 22. During a scan to acquire x-ray projection data, gantry 12 and the components mounted thereon rotate about a center of rotation 24.

Rotation of gantry 12 and the operation of x-ray source 14 are governed by a control mechanism 26 of CT system 10. Control mechanism 26 includes an x-ray controller 28 that provides power and timing signals to x-ray source 14 and a gantry motor controller 30 that controls the rotational speed and position of gantry 12. A data acquisition system (DAS) 32 in control mechanism 26 samples analog data from detector elements 20 and converts the data to digital signals for subsequent processing. An image reconstructor 34 receives sampled and digitized x-ray data from DAS 32 and performs high speed image reconstruction. The reconstructed image is applied as an input to a computer 36 which stores the image in a mass storage device 38. Preferably, the reconstructed image is stored as a data array.

Computer 36 also receives commands and scanning parameters from an operator via console 40 that has a keyboard. An associated display 42, such as a flat panel or a cathode ray tube display, allows the operator to observe the reconstructed image and other data from computer 36. The operator supplied commands and parameters are used by computer 36 to provide control signals and information to DAS 32, x-ray controller 28 and gantry motor controller 30. In addition, computer 36 operates a table motor controller 44 which controls a motorized table 46 to position patient 22 in gantry 12. Particularly, table 46 moves portions of patient 22 through gantry opening 48. As used herein, an Xmm by Xmm scan refers to scanning an object of interest using an X mm collimator aperture at a 1:1 helical pitch, wherein helical pitch is the ratio of table 46 movement in one rotation of the x-ray source 14 to the slice width defined by the source collimator.

To perform multi-slice biopsy scanning, a patient typically is scanned in multiple locations. Particularly, the table speed is ramped up to move a patient to a next location, and then the table speed is ramped down to reach a complete stop. It can also be performed with a helical scan mode. The table speed is ramped up to reach a constant speed for helical scanning, and the table is then ramped down to stop. The table then ramped up in the opposite direction. During the table ramp-up and ramp-down periods, the needle motion can not be updated since no CT scan is performed. Therefore, the image update cycle is 4 seconds at best. In other words, the operator has to wait for at least 4 seconds before the updated information for a certain location is available.

Rather than shuttling the patient back and forth to obtain scans of different locations, the x-ray beams can sweep across the patient. Specifically, by adjusting the positions of a pre-patient collimator, the x-ray beam deviates from the nominal position in z (z is the axis perpendicular to the scan plane). For a mandrel type of collimator, the collimator is rotated with respect to its axis. For collimators having dual blades, the collimator is translated in the z direction. Pre-patient collimators are well known in the art, and the present invention is not limited to practice with any one particular type of pre-patient collimator.

For example, a pre-patient collimator is described in U.S. Pat. No. 5,610,963, which is assigned to present assignee and incorporated herein, in its entirety, by reference. As described in U.S. Pat. No. 5,610,963, the pre-patient collimator is rotatable about its axis, and the angular orientation of the collimator relative to the focal spot affects the profile of the x-ray beam. The collimator is electrically connected to computer 36 (FIG. 2) so that the angular orientation of the collimator can be controlled by computer 36. Known rotatable collimators typically are coupled to a stepper motor which rotates the collimator in multiples of about 0.018°. Energization of the stepper motor is controlled by computer 36 (FIG. 2).

Figure 3:
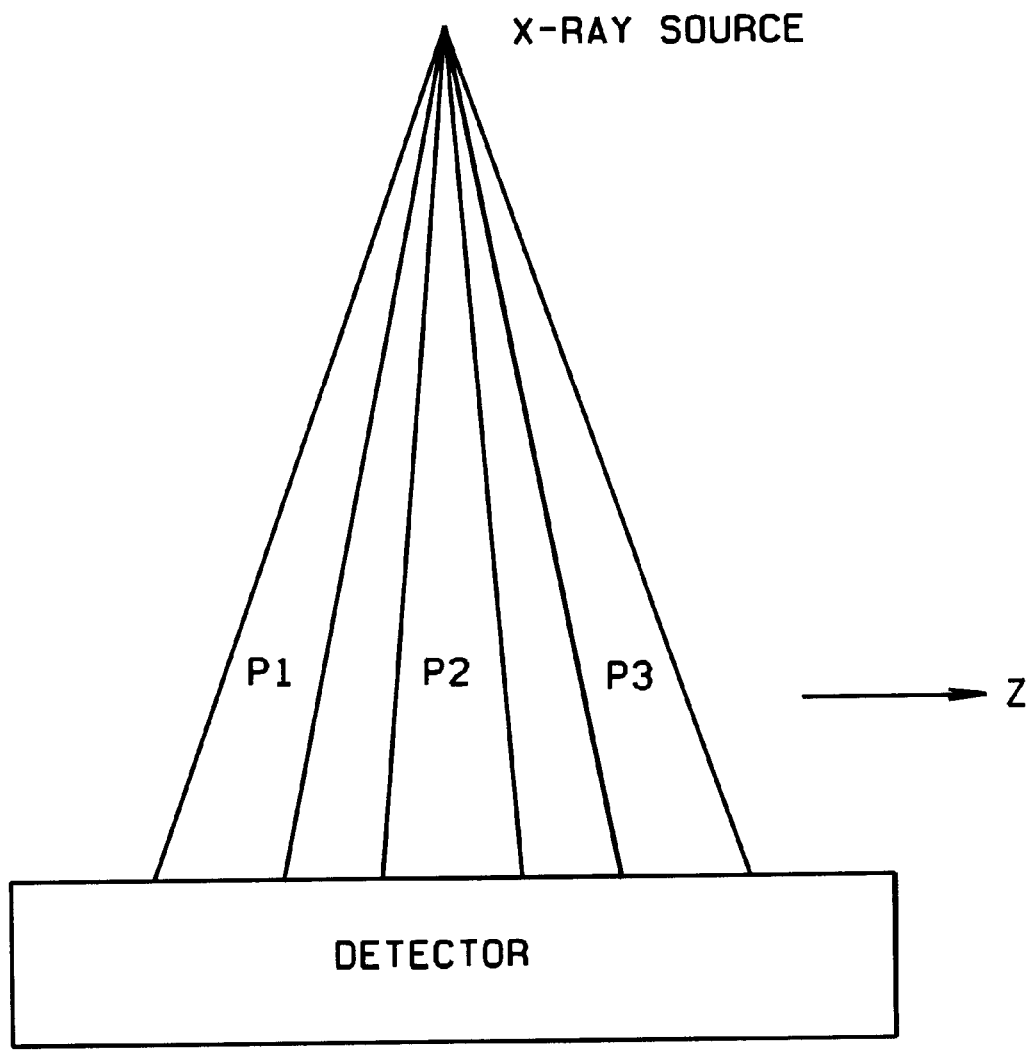
FIG. 3 is a schematic illustration of sweeping an x-ray beam using a pre-patient collimator.

In accordance with one embodiment of the present invention, and referring to FIG. 3, the nominal position of the x-ray beam is shown by a light shaded triangle P2. By modifying the position of the collimator, the x-ray beam can be "deflected" to either to the right or to the left as shown by dark shaded beams P1 and P3. By so deflecting the x-ray beam, a volume can be covered by the x-ray beam without any translation motion of the object.

Because the pre-patient collimator is very light, and because the amount of motion in collimator is very small (due to the large magnification), the x-ray beam deflection can occur instantaneously without any ramp-up or ramp down periods. Therefore, a 100% duty cycle can be achieved and the image update rate may be reduced by a factor of two. Also, no modification to the reconstruction process is necessary. The nominal slice location for each reconstructed image can be easily estimated by the centroid of the beam location during the date acquisition.

Of course, the collimator control can be synchronized, by computer 36, to the fluoro data acquisition so that the desired data is collected. In addition, by controlling the collimator as described above, and even with a single slice detector, a volume scan (not necessarily fluoro) can be performed, i.e., multislice scanner functionality can be achieved with a single slice detector.

From the preceding description of various embodiments of the present invention, it is evident that the objects of the invention are attained. Although the invention has been described and illustrated in detail, it is to be clearly understood that the same is intended by way of illustration and example only and is not to be taken by way of limitation. Accordingly, the spirit and scope of the invention are to be limited only by the terms of the appended claims.

I claim:

1. A method for controlling operation of a pre-patient collimator in a computed tomography system including an x-ray source and a detector during a fluoroscopy scan, said method comprising the steps of:

positioning the collimator in a first position so that an x-ray beam from the x-ray source is oriented in a nominal position on the detector; and deflecting the x-ray beam from the nominal position on the detector.

2. A method in accordance with claim 1 wherein deflecting the x-ray beam from the nominal position comprises the step of adjusting the pre-patient collimator.

3. A method in accordance with claim 2 wherein the pre-patient collimator is a mandrel type collimator.

4. A method in accordance with claim 3 wherein adjusting the pre-patient collimator comprises the step of rotating the collimator.

5. A method in accordance with claim 2 wherein the pre-patient collimator has dual blades.

6. A method in accordance with claim 5 wherein adjusting the pre-patient collimator comprises the step of translating the collimator.

7. A computed tomography system comprising a detector, an x-ray source for projecting an x-ray beam towards said detector, a pre-patient collimator for controlling the orientation of the beam projected from said x-ray source, and a computer coupled to said pre-patient collimator, said computer programmed to:
  position the collimator in a first position so that an x-ray beam from the x-ray source is oriented in a nominal position on the detector; and
  position the collimator in a second position to deflect the x-ray beam from the nominal position on the detector.

8. A computed tomography system in accordance with claim 7 wherein said pre-patient collimator is a mandrel type collimator.

9. A computed tomography system in accordance with claim 8 wherein said computer is programmed to rotate said collimator.

10. A computed tomography system in accordance with claim 7 wherein said pre-patient collimator has dual blades.

11. A computed tomography system in accordance with claim 10 wherein said computer is programmed to translate the collimator.

12. A computed tomography system in accordance with claim 7 further comprising a stepper motor coupled to said pre-patient collimator, and said computer coupled to said stepper motor to control energization of said motor.

13. A computed tomography system in accordance with claim 7 wherein said computer synchronizes position control of said pre-patient collimator with a selected fluoro data acquisition.

14. A computed tomography system for collecting volume data, said system comprising a single slice detector, an x-ray source for projecting an x-ray beam towards said detector, a pre-patient collimator for controlling the orientation of the beam projected from said x-ray source, and a computer coupled to said pre-patient collimator, said computer programmed to:
  position the collimator in a first position so that an x-ray beam from the x-ray source is oriented in a nominal position on the detector; and
  position the collimator in a second position to deflect the x-ray beam from the nominal position on the detector.

15. A computed tomography system in accordance with claim 14 wherein said pre-patient collimator is a mandrel type collimator.

16. A computed tomography system in accordance with claim 15 wherein said computer is programmed to rotate said collimator.

17. A computed tomography system in accordance with claim 14 wherein said pre-patient collimator has dual blades.

18. A computed tomography system in accordance with claim 17 wherein said computer is programmed to translate the collimator.

19. A computed tomography system in accordance with claim 14 further comprising a stepper motor coupled to said pre-patient collimator, and said computer coupled to said stepper motor to control energization of said motor.

20. A computed tomography system in accordance with claim 14 wherein said computer synchronizes position control of said pre-patient collimator with a selected fluoro data acquisition.

* * * * *